US00PP11925P2

(12) United States Plant Patent
Trees

(10) Patent No.: US PP11,925 P2
(45) Date of Patent: Jun. 12, 2001

(54) GERANIUM PLANT NAMED 'BALGALPIPN'

(75) Inventor: Scott C. Trees, Nipomo, CA (US)

(73) Assignee: Ball FloraPlant, a division of Ball Horticultural Co., West Chicago, IL (US)

( * ) Notice: Subject to any disclaimer, the term of this patent is extended or adjusted under 35 U.S.C. 154(b) by 0 days.

(21) Appl. No.: 09/475,966

(22) Filed: Dec. 31, 1999

(51) Int. Cl.[7] ..... A01H 5/00
(52) U.S. Cl. ..... Plt./324

(58) Field of Search ..... Plt./324, 325, 327, Plt./328, 329, 330, 332

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of Geranium plant named 'Balgalpipn', characterized by its semi-double dark pink-colored flowers with reddish purple veins and central spot; large umbels; floriferousness; upright and rounded to spreading growth habit; freely basal-branching growth habit; and good vigor.

1 Drawing Sheet

BACKGROUND OF THE INVENTION

The present invention relates to a new and distinct cultivar of Geranium plant, botanically known as *Pelargonium*× *hortorum*×*P. peltatum*, and hereinafter referred to by the cultivar name 'Balgalpipn'.

The new Geranium is a product of a planned breeding program conducted by the Inventor in Arroyo Grande, Calif. The objective of the breeding program was to develop new cultivars with the combination of the spreading growth habit of Ivy Geraniums with the large spherical umbels of Zonal Geraniums; freely-branching growth habit; medium green-colored leaves; and attractive flower and foliage colors.

The new Geranium originated from an interspecific cross made by the Inventor of the proprietary *Pelargonium*× *hortorum* selection 8936-3 as the male, or pollen parent, with the proprietary *P. peltatum* selection 8543-2 as the female, or seed parent. The cultivar 'Balgalpipn' was discovered and selected by the Inventor as a flowering plant within the progeny of the stated cross in a controlled environment in Arroy Grande in 1997.

Asexual reproduction of the new cultivar by terminal cuttings taken at Arroyo Grande has shown that the unique features of this new Geranium are stable and reproduced true to type in successive generations of asexual reproduction.

SUMMARY OF THE INVENTION

The following traits have been repeatedly observed and are determined to be the unique characteristics of 'Balgalpipn'. These characteristics in combination distinguish 'Balgalpipn' as a new and distinct cultivar:

1. Semi-double dark pink-colored flowers with reddish purple veins and central spot.
2. Large umbels.
3. Very freely flowering.
4. Upright and rounded to spreading growth habit.
5. Freely basal-branching habit and good vigor.

The new Geranium can be compared to the cultivar, 'Pink Passion', disclosed in U.S. Plant Pat. No. 10,396. However, in side-by-side comparisons conducted in Arroyo Grande, plants of the new Geranium differ from plants of the cultivar 'Pink Passion' in the following characteristics:

1. Plants of the new Geranium are more vigorous and larger than plants of the cultivar 'Pink Passion'.
2. Plants of the new Geranium have shorter internodes than plants of the cultivar 'Pink Passion'.
3. Plants of the new Geranium have larger flowers and larger umbels than plants of the cultivar 'Pink Passion'.
4. Plants of the new Geranium have semi-double flowers whereas plants of the cultivar 'Pink Passion' have single flowers.
5. Plants of the new Geranium have solid green leaves whereas plants of the cultivar 'Pink Passion' have zoned leaves.
6. Plants of the new Geranium have smaller leaves than plants of the cultivar 'Pink Passion'.

BRIEF DESCRIPTION OF THE PHOTOGRAPH

The accompanying photograph illustrates the overall appearance of the new cultivar as true as it is reasonably possible to obtain in colored reproductions of this type. Colors in the photographs may differ slightly from the color values cited in the detailed botanical description which accurately describe the actual colors of the new Geranium. The photograph comprises a top perspective view of a typical flowering plant of 'Balgalpipn'.

DETAILED BOTANICAL DESCRIPTION

The cultivar 'Balgalpipn' has not been observed under all possible environmental conditions. The phenotype may vary somewhat with variations in environment such as temperature and light intensity, without, however, any variance in genotype. The following observations and measurements describe plants about 10 weeks after planting rooted cuttings and grown in 10-cm pots in West Chicago, Ill., under commercial practice in a double-layered acrylic-covered greenhouse with day temperatures about 21° C., night temperatures about 19° C., and light levels about 2,500 to 3,500 footcandles.

In the following description, color references are made to The Royal Horticultural Society Colour Chart except where general terms of ordinary dictionary significance are used.

Botanical classification: *Pelargonium×hortorum×P. peltatum* cultivar 'Balgalpipn'.

Parentage:

*Male parent.*—Proprietary *Pelargonium×hortorum* selection 8936-3.

*Female parent.*—Proprietary *Pelargonium peltatum* selection 8543-2.

Propagation:

*Type cutting.*—Terminal cuttings.

*Time to initiate roots.*—About 7 days at temperatures about 18° C.

*Time to develop roots.*—About 21 days at temperatures about 18° C.

*Root description.*—Fibrous and freely branching.

Plant description:

*General appearance.*—Upright and rounded to spreading growth habit. Appropriate for 10 and 12.5-cm containers.

*Crop time.*—Starting with a rooted cutting, about ten weeks are required to produced a finished flowering plant in 10-cm container.

*Growth and branching habit.*—Vigorous and freely basal-branching with about five lateral branches.

*Plant height* (*to top of foliage*).—About 29.8 cm.

*Plant width.*—About 23.9 cm.

*Lateral branches.*—Length: About 24 cm. Internode length: About 2.7 cm. Color: 146C with longitudinal streaks of 182A.

*Foliage description.*—Leaves simple, generally symmetrical, abundant, opposite. Length: About 3.8 cm. Width: About 6.4 cm. Shape: Reniform. Apex: Rounded. Base: Cordate. Margin: Lobed, crenate. Venation: Palmate. Texture: Both surfaces pubescent; leathery. Color: Fully expanded foliage, upper surface: Close to 137A. Fully expanded foliage, lower surface: Close to 137C. Venation, upper surface: Close to 146B. Venation, lower surface: Close to 146B. Zonation: None. Petiole: Length: About 5.6 cm. Diameter: About 2 mm. Color: 146B.

Flower description:

*Flower type and habit.*—Flowers arranged in spherical umbels arising from apical leaf axils. Umbels displayed above or beyond the foliage. At full flowering, usually about five open umbels and about five developing umbels per plant. Flowers semi-double and rounded. Freely and continuously flowering; persistent. Not fragrant.

*Flowering season.*—Year-round under greenhouse conditions. In the garden, flowering is continuous from spring until fall.

*Umbels.*—Number of flowers per umbel: About 12. Diameter: About 9.7 cm. Height: About 6.8 cm.

*Flowers.*—Diameter: About 5.3 cm. Depth (height): About 2.3 cm.

*Flower buds.*—Length: About 1.2 cm. Diameter: About 8 mm. Shape: Rounded to ovoid. Color: Close to 55A.

*Petals/petaloids.*—Quantity: About five petals and about 11 petaloids per flower. Arrangement: Imbricate. Petal length: About 2.8 cm. Petal width: About 2.1 cm. Shape: Petals, obovate; petaloids, irregular. Petal apex: Rounded. Petal base: Attenuate. Petal margin: Entire. Petal texture: Smooth. Color, fully opened flowers: Upper petals and petaloids, upper surface: Background, 54A; lower ⅓ to base, between 54C and 54D with veins of 61B. Towards margin, spot of 61B. Upper petals and petaloids, lower surface: Close to 55A with veins and spot of 54A. Lower petals and petaloids, upper surface: 54A with veins of 61B. Lower petals and petaloids, lower surface: Close to 55A with veins of 54A.

*Sepals.*—Quantity: About seven; somewhat imbricate. Length: About 1 cm. Shape: Linear. Apex: Acuminate. Margin: Entire. Texture: Pubescent. Color: Upper surface: 145A; base, 177A. Lower surface: 145A with streaks of 177A; base, 177A.

*Peduncle* (*umbel stem*).—Length: About 18.3 cm. Angle: Erect. Strength: Strong. Texture: Scabrous. Color: Mixture of 178A and 146B.

*Pedicel* (*individual flower stem*).—Length: About 2.4 cm. Angle: Upright or outward. Strength: Strong. Texture: Puberulent. Color: 177A.

*Reproductive organs.*—Androecium: Anther size: About 3 mm. Pollen: Scarce. Pollen Color: Close to 28A. Gynoecium: Pistil number: One. Ovary color: Green.

Disease resistance: Plants of the new Geranium have not been observed to be resistant to pathogens common to Pelargonium.

Seed development: Seed production has not been observed.

It is claimed:

1. A new and distinct cultivar of Geranium plant named 'Balgalpipn', as illustrated and described.

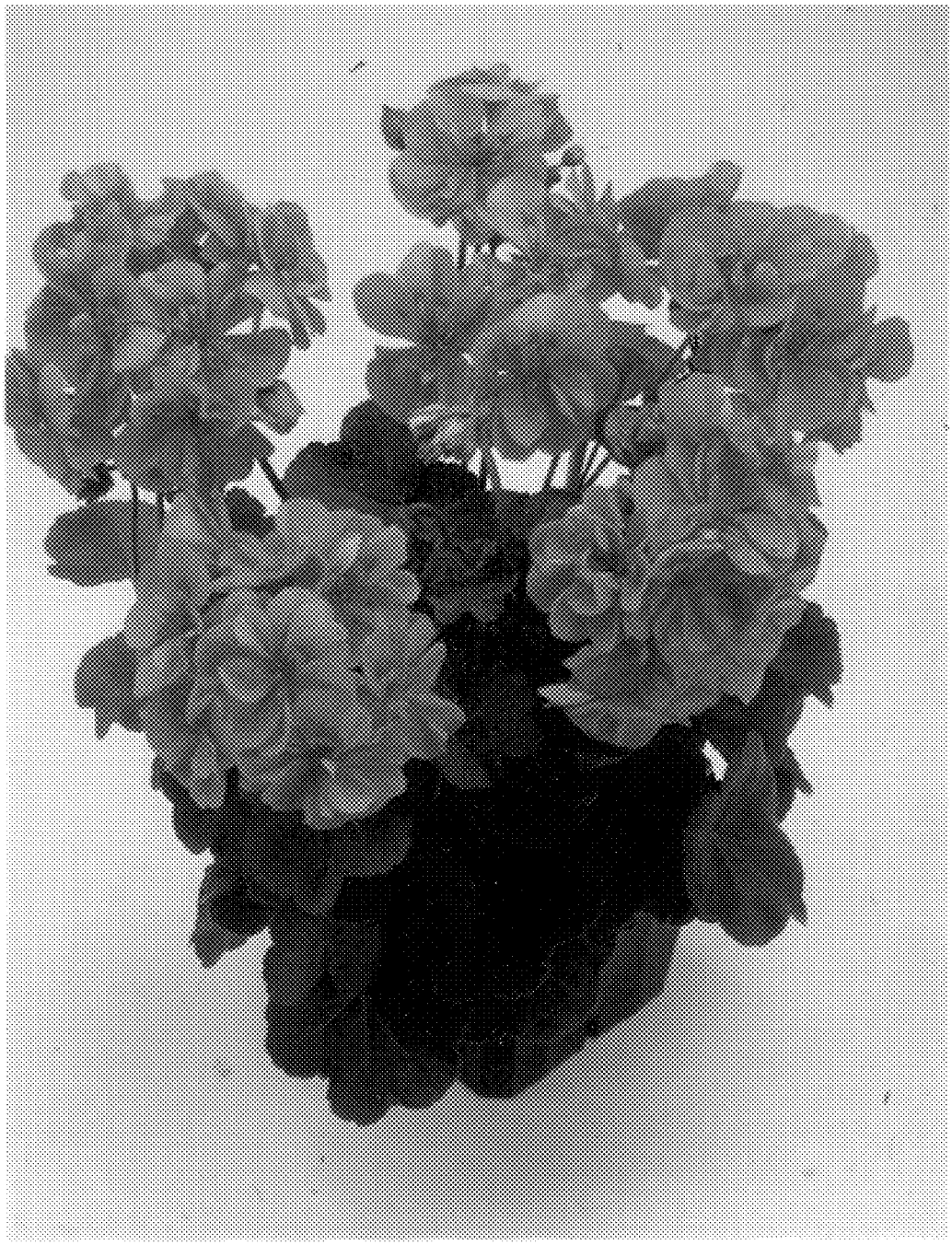

* * * * *